United States Patent [19]

Nakanishi

[11] Patent Number: 5,039,683
[45] Date of Patent: Aug. 13, 1991

[54] AZETIDINYL QUINOLONE CARBOXYLIC ACIDS AND ESTERS

[75] Inventor: Susumu Nakanishi, Niantic, Conn.

[73] Assignee: Pfizer Inc., New York, N.Y.

[21] Appl. No.: 365,156

[22] PCT Filed: Oct. 26, 1987

[86] PCT No.: PCT/US87/02792
§ 371 Date: May 31, 1989
§ 102(e) Date: May 31, 1989

[87] PCT Pub. No.: WO89/03828
PCT Pub. Date: May 5, 1989

[51] Int. Cl.$^5$ ............................................. A61K 31/47
[52] U.S. Cl. ................................... 514/312; 544/100; 546/156; 546/170; 548/537
[58] Field of Search .................. 544/100; 546/156, 152; 514/170, 311, 312, 210; 548/537

[56] References Cited

U.S. PATENT DOCUMENTS

| | | | |
|---|---|---|---|
| 4,665,079 | 5/1987 | Culbertson et al. | 514/256 |
| 4,670,444 | 6/1987 | Grohe et al. | 546/156 |

FOREIGN PATENT DOCUMENTS

| | | | |
|---|---|---|---|
| 0153163 | 2/1985 | European Pat. Off. | 514/312 |
| 60089480 | 5/1985 | Japan. | |
| 61137885 | 6/1986 | Japan. | |
| 61152682 | 7/1986 | Japan. | |
| 61282382 | 12/1986 | Japan. | |
| 62019883 | 1/1987 | Japan. | |
| 62-030776 | 2/1987 | Japan. | |
| 6230776 | 2/1987 | Japan | 546/156 |

OTHER PUBLICATIONS

Iwata et al., Chemical Abstracts, vol. 10, p. 701, 135095v.
Egawa et al., J. Med. Chem., 27, 1543-8 (1984).

Primary Examiner—Jose G. Dees
Assistant Examiner—Deborah D. Cair
Attorney, Agent, or Firm—Peter C. Richardson; Paul H. Ginsburg; Valerie M. Fedowich

[57] ABSTRACT

Compounds of the formula

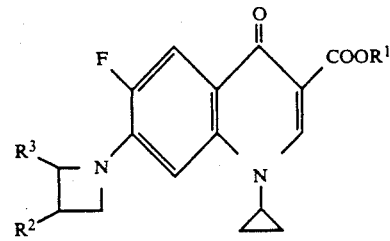

wherein $R^1$ is hydrogen, alkyl of 1 to 6 carbon atoms, or $NR^4R^5$, wherein $R^4$ and $R^5$ are independently selected from hydrogen and alkyl of 1 to 6 carbon atoms or a pharmaceutically acceptable cation;

$R^2$ is hydrogen, hydroxy, alkanoylamino of 1 to 6 carbon atoms, morpholino, halogen, hydroxyalkyl of 1 to 6 carbon atoms, $COOR^6$ wherein $R^6$ is alkyl of 1 to 6 carbon atoms or a pharmaceutically acceptable cation, alkoxy of 1 to 6 carbon atoms, $NR^7R^8$ wherein $R^7$ and $R^8$ are independently selected from alkyl of 1 to 6 carbon atoms, alkanoyl of 1 to 6 carbon atoms, hydrogen, alkoxy of 1 to 6 carbon atoms, aminoalkyl of 2 to 6 carbon atoms, alkylaminoalkyl wherein each alkyl group is independently selected from alkyl groups having 2 to 6 carbon atoms, and dialkylaminoalkyl wherein each alkyl group is independently selected from alkyl groups having one to six carbon atoms, with the proviso that only one of $R^7$ and $R^8$ may be alkoxy; and $R^3$ is hydrogen, alkyl of 1 to 6 carbon atoms, phenyl or substituted phenyl wherein the phenyl group may be substituted with one or two substituents selected from the group consisting of alkyl of 1 to 6 carbon atoms, nitro, amino, halogen, (e.g., fluoro, chloro, bromo, or iodo), haloalkyl of 1 or 2 carbon atoms and up to 5 halogen atoms (e.g., fluoro, chloro, bromo or iodo), hydroxyl, or alkoxy of 1 to 6 atoms and pharmaceutically acceptable acid addition salts thereof. The compounds have antibacterial activity.

20 Claims, No Drawings

AZETIDINYL QUINOLONE CARBOXYLIC ACIDS AND ESTERS

BACKGROUND OF THE INVENTION

This invention relates to azetidinyl quinolone carboxylic acids and esters, antibacterial compositions containing said compounds, methods of using said compounds, and methods of preparing said compounds.

U.S. Pat. No. 4,563,459 refers to 1-cyclopropyl-1,4-dihydro-4-oxo-quinoline carboxylic acids wherein the moiety in the 6-position is hydrogen, fluorine, chlorine, bromine or nitro and the moiety in the 7-position is hydrogen, chlorine, fluorine or $NR^3R^4$ wherein $R^3$ and $R^4$ represent separate groups or, together with the nitrogen atom on which they are positioned, may form a 5-membered or 6-membered heterocyclic ring.

Japanese Kokai SHO 60-89480 refers to compounds of the formula

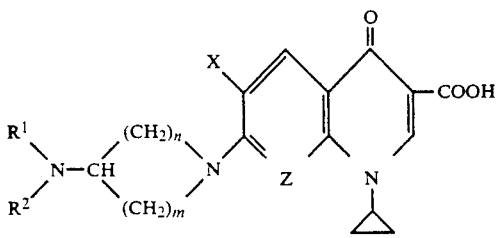

wherein Z is nitrogen or CH; X is halogen;
$R^1$ and $R^2$ are hydrogen, acyl or lower alkyl;
m is 1 or 2; and n is 1, 2 or 3. However, no specific quinoline compounds are disclosed.

SUMMARY OF THE INVENTION

The present invention relates to compounds of the formula

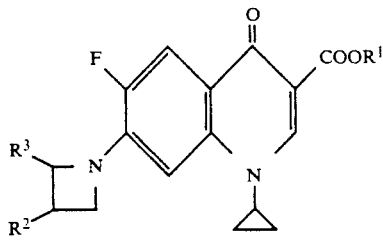

wherein $R^1$ is hydrogen, alkyl of 1 to 6 carbon atoms, or $NR^4R^5$ wherein $R^4$ and $R^5$ are independently selected from hydrogen and alkyl of 1 to 6 carbon atoms or a pharmaceutically acceptable cation;

$R^2$ is hydrogen, hydroxy, alkanoylamino of 1 to 6 carbon atoms, morpholino, halogen, hydroxyalkyl of 1 to 6 carbon atoms, $COOR^6$ wherein $R^6$ is alkyl of 1 to 6 carbon atoms or a pharmaceutically acceptable cation, alkoxy of 1 to 6 carbon atoms, $NR^7R^8$ wherein $R^7$ and $R^8$ are independently selected from alkyl of 1 to 6 carbon atoms, alkanoyl of 1 to 6 carbon atoms, hydrogen, alkoxy of 1 to 6 carbon atoms, aminoalkyl of 2 to 6 carbon atoms, alkylaminoalkyl wherein each alkyl group is independently selected from alkyl groups having 2 to 6 carbon atoms, and dialkylaminoalkyl wherein each alkyl group is independently selected from alkyl groups having one to six carbon atoms, with the proviso that only one of $R^7$ and $R^8$ may be alkoxy; and $R^3$ is hydrogen, alkyl of 1 to 6 carbon atoms, phenyl or substituted phenyl wherein the phenyl group may be substituted with one or two substituents selected from the group consisting of alkyl of 1 to 6 carbon atoms, nitro, amino, halogen (e.g., fluoro, chloro, bromo, or iodo), haloalkyl of 1 or 2 carbon atoms and up to 5 halogen atoms (e.g., fluoro, chloro, bromo or iodo), hydroxyl, or alkoxy of 1 to 6 atoms and pharmaceutically acceptable acid addition salts thereof. The compounds have antibacterial activity.

The present invention also relates to pharmaceutical compositions comprising a pharmaceutically acceptable carrier or diluent and a compound of the formula I or a pharmacutically acceptable salt thereof in an antibacterially effective amount. The present invention also provides a method of treating an animal, including a human being, having a bacterial disease which comprises administering to the animal (e.g., mammal, bird or fish) an antibacterially effective amount of a compound of the formula I or a pharmaceutically acceptable acid addition salt thereof. The present invention also relates to methods of preparing the compounds of formula I.

The compounds of the invention include racemic mixtures and optical isomers. Preferred compounds of the invention are those of formula I wherein $R^1$ is hydrogen, a pharmaceutically acceptable cation (e.g., sodium or potassium), or amino. Other preferred compounds are those of formula I wherein $R^2$ is hydrogen, amino, hydroxy, hydroxymethyl, acetylamino or $COOR^6$, wherein $R^6$ is hydrogen, a pharmaceutically acceptable cation, or amino. Other preferred compounds are those of formula I wherein $R^3$ is hydrogen or phenyl. More preferred compounds are those wherein $R^1$ is hydrogen, a pharmaceutically acceptable cation, or amino; $R^2$ is hydrogen, amino, or hydroxy and $R^3$ is hydrogen or phenyl. Specific preferred compounds are as follows:

1-cyclopropyl-6-fluoro-1,4-dihydro-7-[1'-azetidinyl]-4-oxo-3-quinoline-carboxylic acid;

1-cyclopropyl-6-fluoro-1,4-dihydro-7-[3'hydroxy-1'-azetidinyl]-4-oxo-3-quinoline-carboxylic acid;

1-cyclopropyl-6-fluoro-1,4-dihydro-7-[3'amino-1'-azetidinyl]-4-oxo-3-quinoline-carboxylic acid; and 1-cyclopropyl-6-fluoro-1,4-dihydro-7-[3'-acetylamino-1'-azetidinyl]-4-oxo-3-quinoline-carboxylic acid.

The pharmaceutical compositions of the present invention preferably contain the above preferred and specific preferred compounds.

Other compounds of the present invention are the following:

1-cyclopropyl-6-fluoro-1,4-dihydro-7-[2'-phenyl3'-amino-1'-azetidinyl]-4-oxo-3-quinoline-carboxylic acid;

1-cyclopropyl-6-fluoro-1,4-dihydro-7-[2'-methyl-3'-hydroxy-1'-azetidinyl]-4-oxo-3-quinoline-carboxylic acid;

1-cyclopropyl-6-fluoro-1,4-dihydro-7-[2'-methyl-3'amino-1'-azetidinyl]-4-oxo-3-quinoline-carboxylic acid;

1-cyclopropyl-6-fluoro-1,4-dihydro-7-[3'-carboxyl-1'-azetidinyl]-4-oxo-3-quinoline-carboxylic acid;

1-cyclopropyl-6-fluoro-1,4-dihydro-7-[3'-cyano-1'-azetidinyl]-4-oxo-3-quinoline-carboxylic acid;

1-cyclopropyl-6-fluoro-1,4-dihydro-7-[2'-ethyl-3'-hydroxy-1'-azetidinyl]-4-oxo-3-quinoline-carboxylic acid;

1-cyclopropyl-6-fluoro-1,4-dihydro-7-[2'-propyl-3'amino-1'-azetidinyl]-4-oxo-3-quinoline-carboxylic acid;

1-cyclopropyl-6-fluoro-1,4-dihydro-7-[3'-hydroxymethyl-1'-azetidinyl]-4-oxo-3-quinoline-carboxylic acid;

1-cyclopropyl-6-fluoro-1,4-dihydro-7-[3'-aminomethyl-1'-azetidinyl]-4-oxo-3-quinoline-carboxylic acid.

DETAILED DESCRIPTION OF THE INVENTION

The compounds of the present invention may be prepared by reacting a quinolone of the formula

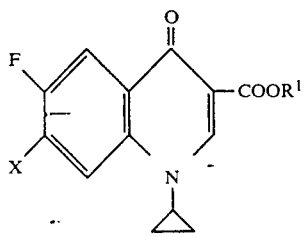

wherein R¹ is as defined above and X is fluoro, chloro, bromo or iodo (preferably, fluoro or chloro; more preferably, fluoro) with an amine of the formula

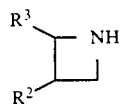

wherein R² and R³ are as defined above, in an inert solvent or in a basic solvent. Examples of suitable solvents are tetrahydrofuran, pyridine, ethanol, chloroform, dimethylsulfoxide, dimethylformamide, water and mixtures thereof. If the solvent is not a basic solvent such as, for example, pyridine, it is desirable to add a base to the reaction mixture. The base serves to facilitate completion of the reaction by reacting with the hydrogen fluoride that is produced in the reaction. The addition of DBU (which is a strong base) to the reaction mixture is preferred. A preferred solvent is a mixture of acetonitrile and 1,8-diazabicyclo(5.4.0) - undec.-7-ene(DBU). Especially preferred, is acetonitrile solvent containing 1 to 3 equivalents of DBU. The temperature and pressure are not critical. Generally, however, a temperature of 30 to 100° C. and a pressure of 0.5 to 2 atmospheres are preferred. More preferably, the pressure is ambient pressure (generally, about 1 atmosphere). Although a significant amount of product may be formed in about 5 minutes, the reaction is generally allowed to proceed overnight. The product is isolated by conventional methods. For example, the product may be isolated by adding water to the reaction mixture, adjusting the pH to 7.0-7.4, collecting the resulting precipitate by filtration and then water washing and drying the precipitate. Using conventional methods, compounds of the present invention wherein R¹ is other than hydrogen may be prepared by converting a compound of the formula I wherein R¹ is hydrogen to the corresponding ester or amide. Alternatively, a compound of the formula II wherein R¹ is hydrogen may be converted to the corresponding ester or amide by conventional methods and that ester or amide may then be used to prepare a compound of the formula I as described above.

Compounds of the formula II may be prepared as described in U.S. Pat. No. 4,563,459.

Amines or alcohols of the formula III may be prepared by well known methods. See, for example, T. Okutani et al., *Chem. Pharm. Bull.*, 22, 1490–1497 (1974); S. Chatterjee et al., *Chem. Comm.*, 93 (1968); D. Nisato et al., *J. Heterocyclic Chem.*, 22, 961 (1985); I. Hayakawa et al., *Chem. Pharm. Bull.*, 32, 4907–4913 (1984); A. G. Anderson et al., *J. Org. Chem.*, 37, 3953–3955 (1972); and V. R. Gaertner, *J. Org. Chem.*, 32, 2972–2976 (1967). Thus, for example 2-phenyl and 2-substituted phenyl-3-amino-azetidines may be prepared by the method of T. Okutani et al. and 3-hydromethyl-1-azetidine may be prepared by the method of I. Hayakawa et al.

The pharmaceutically acceptable acid addition salts of the compounds of the formula I are prepared in a conventional manner by treating a solution or suspension of the free base of the formula I with about one chemical equivalent of a pharmaceutically acceptable acid. Conventional concentration and recrystallization techniques are employed in isolating the salts. Illustrative of suitable acids are acetic, lactic, succinic, maleic, tartaric, citric, gluconic, ascorbic, benzoic, methanesulfonic, cinnamic, fumaric, phosphonic, hydrochloric, hydrobromic, hydroidic, sulfamic and sulfonic acid.

The pharmaceutically acceptable cationic salts of formula I may be prepared by conventional methods from the corresponding acids, e.g., by reaction with about one equimolar amount of a base. Examples of suitable cationic salts are those of alkali metals such as sodium or potassium, alkaline earth metals such as magnesium or calcium, and ammonium or organic amines such as diethanol amine or N-methyl-glucamine.

The compounds of formula I and the pharmaceutically acceptable acid addition salts thereof are broad spectrum antibacterials useful in the treatment of bacterial infections, particularly the treatment of infections of gram-positive bacterial strains.

The compounds of the present invention may be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals (for example, swine, cattle, horses, and poultry), they are advantageously contained in an animal feed or drinking water in a concentration of about 5 to about 5000 ppm, preferably about 25 to about 500 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, compounds can be administered intramuscularly or subcutaneously at dosage levels of about 0.1 to about 50 mg/kg/day, advantageously about 0.2 to about 10 mg/kg/day, given in a single daily dose or up to 3 divided doses.

The invention also provides pharmaceutical compositions comprising an antibacterially effective amount of a compound of the formula I or a pharmaceutically acceptable acid addition salt thereof together with a pharmaceutically acceptable diluent or carrier.

The compounds of the present invention can be administered to humans for the treatment of bacterial diseases by either the oral or parenteral routes, and may be administered orally at dosage levels of about 0.1 to about 500 mg/kg/day, advantageously about 0.5 to about 50 mg/kg/day, given in a single dose or up to 3 divided doses. For intramuscular or intravenous administration, dosage levels are about 0.1 to about 200 mg/kg/day, advantageously about 0.5 to about 50 mg/kg/day. Intramuscular administration may be accomplished with a single dose or up to 3 divided doses. Intravenous administration may be accomplished with a continuous drip. Variations will necessarily occur depending on the weight and condition of the subject being treated and the particular route of administration chosen as will be known to those skilled in the art.

The antibacterial activity of the compounds of the invention is shown by testing according to the Steer's replicator technique which is a standard in vitro bacterial testing method described by E. Steers et al., *Antibiotics and Chemotherapy*, 9, 307 (1959).

The following non-limiting Examples illustrate the invention. All melting points referred to in the Examples are uncorrected.

EXAMPLE 1

1-cyclopropyl-6-fluoro-1,4-dihydro-7-[1'-azetidinyl]-4-oxo-3-quinoline-carboxylic acid A mixture of 1-cyclopropyl-6,7-difluoro-1,4-dihydro-4-oxo-quinoline-3-carboxylic acid (1.591 g, 6 mmole), acetonitrile (70 ml), azetidine (390 mg, 6.8 mmole) and DBU (913 mg, 6 mmole) were heated at reflux. After only 5 minutes of heating, it was observed that crystalline material was precipitating. After 5 additional minutes of heating, the hot solution was filtered. The reaction mixture was then allowed to cool at room temperature for 1 hour. The solid material that precipitated was collected by filtration, washed first with acetonitrile and then with ethyl ether and then dried to give 650 mg of the title compound, m.p. 298°–299° C. (dec.). NMR(DMSO-D6): 1.12–1.13 d and 1.26–1.28 d, 4H of cyclopropane; 2.3–2.4, m, 2H of $C_3'$ azetidine; 3.2–3.7, q, 1H of cyclopropane; 4.19–4.24, q, 4H of azetidine $C_2'$ and $C_4'$; 6.82–6.85, d, 1H of $C_8$; 7.74–7.78, d, 1H of $C_5$; 8.55, s, 1H of $C_2$.

A second crop of crystals was obtained and was washed and dried as described above to give 210 mg of the title compound, m.p. 297°–299° C. (dec.). The combined yield was 48%.

EXAMPLE 2

1-cyclopropyl-6-fluoro-1,4-dihydro-7-[3'-amino-1'-azetidinyl]-4-oxo-3-quinoline-carboxylic acid and its hydrochloride salt A mixture of 3-amino-1-azetidine (80 mg, 0.048 mmole), 1-cyclopropyl-6,7-difluoro-1,4-dihydro-4-oxo-quinoline-3-carboxylic acid (10.6 mg, 0.04 mole) and DBU (0.0113 ml, 12.1 mg, 0.08 mmole) in 5 ml of acetonitrile was refluxed under nitrogen (79°–80° C.) for 3 hours and was then allowed to stand at room temperature under nitrogen overnight. The reaction mixture was then filtered and the wet cake was washed with acetonitrile and then with ethyl ether. The cake was then dried in vacuo to give 15 mg of the title compound, m.p. 277°–278° C.

The hydrochloride salt of the title compound was prepared by adding 130 mg (0.04 mmole) of the title compound to methanolic HCl containing an equivalent amount (0.04 mmole) of HCl and stirring at room temperature for 4 hours. Crystals were collected by filtration, washed with ethyl ether and dried to give 22.3 mg of the hydrochloride salt, m.p. above 300° C. NMR (DMSO-D6): 1.12–1.13, d, and 1.26–1.28 d, 4H of cyclopropane, 3.8, s, 1H of cyclopropane; 4.05–4.25, m, 4H of $C_2'$ and $C_4'$ azetidine; 4.46–4.52, q, 1H of azetidine $C_3'$; 6.92–6.98, d, 1H of $C_8$; 7.80–7.86, d, 1H of $C_5$; 8.6, s, 1H of $C_2$; 8.68–8.84, d, 2H of $NH_2$.

EXAMPLE 3

1-Cylopropyl-6-fluoro-1,4-dihydro-7-[3'-hydroxy-1'-azetidinyl]-4-oxo-3-quinoline-carboxylic acid A mixture of 3-hydroxy-1-azetidine hydrochloride (120 mg, 1.1 mmole), 1-cyclopropyl-6,7-difluoro 1,4-dihydro-4-oxo-quinoline-3-carboxylic acid (265 mg, 1 mmole) and 299 ml (2 mmole) of DBU in 10 ml of acetonitrile was refluxed under nitrogen for 2.5 hours and was then filtered hot. The wet cake was washed with acetonitrile and dried to give 130 mg of the title compound, m.p. 294°–295° C. (dec.).

EXAMPLE 4

1-Cylopropyl-6-fluoro-1,4-dihydro-7-[3'-carboxyl-1'azetidinyl]-4-oxo-3-quinoline-carboxylic acid and its 3'-sodium carboxylate A mixture of 1-cyclopropyl-6,7-difluoro-1,4-dihydro-4-oxo-quinoline-3-carboxylic acid (132.5 mg, 0.005 mmole), azetidine-3-carboxylic acid (55.6 mg, 0.055 mmole) and DBU (0.075 ml, 0.05 mmole) in 5 ml of acetonitrile was refluxed under nitrogen for 2 hours. The reaction mixture was then allowed to cool at room temperature for 2 hours. The resulting solid was suspended in 3 ml of water and the pH was adjusted to 8.5 by the addition of saturated aqueous $NaHCO_3$ solution. Ethyl ether was then added. The resulting mixture was shaken in a separatory funnel and the organic layer was separated. The aqueous layer was filtered and the filtered solution was freeze dried overnight to yield 180 mg (92%) of the title compound as the disodium salt, m.p. 287°–289° C. (dec.).

EXAMPLE 5

1-Cyclopropyl-6-fluoro-1,4-dihydro-7-[3'-acetylamino-1'-azetidinyl]-4-oxo-3-quinoline-carboxylic acid and its hydrochloride salt A mixture of 3-acetylamino-1-azetidine (110 mg, 0.963 mmole), 1-cyclopropyl-6,7-difluoro-1,4-dihydro-4-oxo-quinoline-3-carboxylic acid (212 mg, 0.8 mmole) and DBU (0.134 ml, 137 mg, 0.9 mmole) in 10 ml of acetonitrile were refluxed under nitrogen (79°–80° C.) for one hour and was then allowed to stand at room temperature under nitrogen overnight. The reaction mixture was then filtered and the wet cake was washed with acetonitrile and then with ethyl ether. The cake was then dried in vacuo to give 311 mg of the title compound.

The hydrochloride salt was prepared by adding the title compound (100 mg) to methanolic HCl containing an equivalent amount of HCl and stirring at room temperature for 30 minutes. The solid material that formed was filtered, washed with acetonitrile, and dried in vacuo to give 83.7 mg (76%) of the hydrochloride salt, m.p. 265°–266° C. dec.

EXAMPLE 6

1-Cyclopropyl-6-fluoro-1,4-dihydro-7-[2'-methyl-3'hydroxy-1'-azetidinyl]-4-oxo-3-quinoline-carboxylic acid Following the method of Example 1, but employing 2-methyl-3-hydroxy-1-azetidine in place of azetidine, there was obtained the title compound, m.p. above 300° C.

EXAMPLE 7

1-Cyclopropyl-6-fluoro-1,4-dihydro-7-[3'-hydroxymethyl-1'-azetidinyl]-4-oxo-3-quinoline-carboxylic acid A mixture of 3-hydroxymethyl-1-azetidine 4.4 mg, 0.05 mmole), 1-cyclopropyl-6,7-difluoro-1,4-dihydro-4-oxo-quinoline-3-carboxylic acid (10.6 mg, 0.04 mmole) and DBU (0.0113 ml, 12.1 mg, 0.08 mmole) in 5 ml of acetonitrile was refluxed under nitrogen for 3 hours and was then allowed to stand at room temperature under nitrogen overnight. The reaction mixture was then filtered, and the wet cake was washed with acetonitrile and dried in vacuo to give 9.9 mg (59%) of the title compound, m.p. about 300° C.

EXAMPLE 8

1-Cyclopropyl-6-fluoro-1,4-dihydro-7-[2'-phenyl-3'-amino-1'-azetidinyl]-4-oxo-3-quinoline carboxylic acid 2-phenyl-3-amino-1-azetidine dihydrochloride (9.24 mg, 0.05 mmole), 1-cyclopropyl-6,7-difluoro-1,4-dihydro-4-oxo-quinoline-3-carboxylic acid (10.6 mg, 0.04 mmole) and DBU (12.1 mg, 0.08 mmole) in 5 ml of acetonitrile was refluxed for 8 hours and then allowed to stand at room temperature overnight under nitrogen. The mixture was then filtered, washed with acetonitrile and dried in vacuo to give 6.3 mg (40%), m.p. above 300° C.

EXAMPLE 9

The title compounds of Examples 1, 2, 3 and 5 were tested for in vitro antibacterial activity using the Steer's replicator technique. The compounds were found to be active against *Staphlococcus aureus, 'Staphylococcus epidermis, Streptococcus pyogenes, Escherichia coli, Klebsiella pneumoniae, Klebsiella oxytoca, Pasteurella multocida, Serratia marcescens, Neisseria sicca, Enterobacter aerogenes, Enterobacter cloacae,* and *Morganella morganii* at levels lower than 3.2 micrograms per ml.

I claim:
1. A compound of the formula

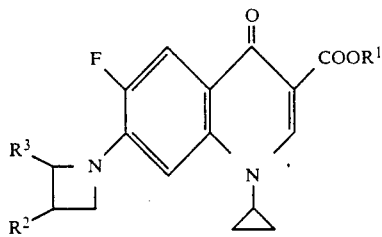

wherein $R^1$ is hydrogen, alkyl of 1 to 6 carbon atoms, or $NR^4R^5$, wherein $R^4$ and $R^5$ are independently selected from hydrogen and alkyl of 1 to 6 carbon atoms or a pharmaceutically acceptable cation;

$R^2$ is hydrogen, hydroxy, alkanoylamino of 1 to 6 carbon atoms, morpholino, halogen, hydroxyalkyl of 1 to 6 carbon atoms, $COOR^6$ wherein $R^6$ is alkyl of 1 to 6 carbon atoms or a pharmaceutically acceptable cation, alkoxy of 1 to 6 carbon atoms, $NR^7R^8$ wherein $R^7$ and $R^8$ are independently selected from alkyl of 1 to 6 carbon atoms, alkanoyl of 1 to 6 carbon atoms, hydrogen, alkoxy of 1 to 6 carbon atoms, aminoalkyl of 2 to 6 carbon atoms, alkylaminoalkyl wherein each alkyl group is independently selected from alkyl groups having 2 to 6 carbon atoms, and dialkylaminoalkyl wherein each alkyl group is independently selected from alkyl groups having one to six carbon atoms, with the proviso that only one of $R^7$ and $R^8$ may be alkoxy; and $R^3$ is hydrogen, alkyl of 1 to 6 carbon atoms, phenyl or substituted phenyl wherein the phenyl group may be substituted with one or two substituents selected from the group consisting of alkyl of 1 to 6 carbon atoms, nitro, amino, halogen, haloalkyl of 1 or 2 carbon atoms and up to 5 halogen atoms, hydroxyl, or alkoxy of 1 to 6 atoms and pharmaceutically acceptable acid addition salts thereof.

2. A compound according to claim 1, wherein $R^2$ is hydrogen, amino, hydroxy, acetylamino, hydroxymethyl, or $COOR^6$ wherein $R^6$ is hydrogen, a pharmaceutically acceptable cation or amino.

3. A compound according to claim 1, wherein $R^1$ is hydrogen, a pharmaceutically acceptable cation or amino.

4. A compound according to claim 1, wherein $R^1$ is an alkali metal or alkaline earth metal cation.

5. A compound according to claim 1, wherein $R^6$ is an alkali metal or alkaline earth metal cation.

6. A compound according to claim 1 wherein $R^2$ is hydrogen, amino or hydroxy and $R^3$ is hydrogen or phenyl.

7. A compound according to claim 6 wherein $R^1$ is hydrogen, a pharmaceutically acceptable cation or amino.

8. A compound according to claim 1, said compound being selected from the group consisting of
1-cyclopropyl-6-fluoro-1,4-dihydro-7-[1'-azetidinyl]-4-oxo-3-quinolinecarboxylic acid;
1-cyclopropyl-6-fluoro-1,4-dihydro-7-[3'-hydroxy-1'-azetidinyl]- 4-oxo-3-quinolinecarboxylic acid;
1-cyclopropyl-6-fluoro-1,4-dihydro-7-[3'-amino-1'-azetidinyl]-4-oxo-3-quinolinecarboxylic acid;
1-cyclopropyl-6-fluoro-1,4-dihydro-7-[3'-acetylamino-1'-azetidinyl]- 4-oxo-3-quinolinecarboxylic acid;
1-cyclopropyl-6-fluoro-1,4-dihydro-7-[2'-methyl3'-amino-1'-azetidinyl]-4-oxo-3-quinolinecarboxylic acid;
1-cyclopropyl-6-fluoro-1,4-dihydro-7-[2'-phenyl-3-amino-1'-azetidinyl)-4-oxo-3-quinolinecarboxylic acid; and pharmaceutically acceptable acid addition salts of the foregoing compounds.

9. An antibacterial composition comprising a compound according to claim 1 in an amount sufficient for treatment of a bacterial infection, and a pharmaceutically acceptable carrier.

10. A composition according to claim 9, wherein $R^2$ is hydrogen, amino, hydroxy, acetylamino, hydroxymethyl, $COOR^6$, wherein $R^6$ is hydrogen a pharmaceutically acceptable cation, or amino.

11. A composition according to claim 10, wherein $R^1$ is hydrogen, a pharmaceutically acceptable cation or amino.

12. A composition according to claim 9, wherein $R^1$ is an alkali metal or alkaline earth metal cation.

13. A composition according to claim 9, wherein $R^6$ is an alkali metal or alkaline earth metal cation.

14. A composition according to claim 9, wherein $R^2$ is hydrogen, amino or hydroxy and $R^3$ is hydrogen or phenyl.

15. A composition according to claim 14, wherein $R^1$ is hydrogen, a pharmaceutically acceptable cation or amino.

16. A method for the treatment of bacterial infection which comprises administering to a subject in need of treatment an antibacterially effective amount of a compound according to claim 1.

17. A method according claim 16, wherein $R^2$ is hydrogen, amino, hydroxy, acetylamino, hydroxymethyl, or $COOR^6$ wherein $R^6$ is hydrogen, a pharmaceutically acceptable cation, or amino.

18. A method according to claim 16, wherein $R^1$ is hydrogen, a pharmaceutically acceptable cation or amino.

19. A method according to claim 16, wherein $R^2$ is hydrogen, amino or hydroxy and $R^3$ is hydrogen or phenyl.

20. A method according to claim 19, wherein $R^1$ is hydrogen, a pharmaceutically acceptable cation or amino.

* * * * *